United States Patent [19]

Rainin

[11] Patent Number: 5,599,330
[45] Date of Patent: Feb. 4, 1997

[54] SURGICAL WICKING DEVICE

[76] Inventor: Edgar A. Rainin, 111 Wild Oak Ct., Danville, Calif. 94526

[21] Appl. No.: 306,173

[22] Filed: Sep. 14, 1994

Related U.S. Application Data

[63] Continuation-in-part of Ser. No. 156,584, Nov. 23, 1993, abandoned.

[51] Int. Cl.$^6$ ................................................. A61M 1/00
[52] U.S. Cl. ........................ 604/317; 604/1; 604/289; 604/315; 604/902
[58] Field of Search ............................. 604/1, 23, 313, 604/315, 317, 289, 294, 48, 902; 128/755

[56] References Cited

U.S. PATENT DOCUMENTS

| | | | |
|---|---|---|---|
| 3,394,702 | 7/1968 | Heimlich et al. | 604/1 |
| 3,443,562 | 5/1969 | Gustafson | 604/1 |
| 5,085,633 | 2/1992 | Hanifl et al. | 604/35 |
| 5,407,423 | 4/1995 | Yoon | 604/1 |
| 5,451,204 | 9/1995 | Yoon | 604/1 |

*Primary Examiner*—John G. Weiss
*Assistant Examiner*—Mark O. Polutta
*Attorney, Agent, or Firm*—Bielen, Peterson & Lampe

[57] ABSTRACT

A surgical wicking device utilizing a hollow conduit having a first end portion and a second portion terminating in an open end. The first end portion is connected to a suction source. A porous element having an outer surface and a matrix within the same is capable of transporting fluids, including blood, from the outer surface to a inner or central reservoir or zone of the matrix by only capillary flow. The open end of the second end portion of the hollow flexible conduit is held to the interior of porous element adjacent the matrix inner zone, to permit aspiration of fluids from the matrix central zone to the conduit.

8 Claims, 1 Drawing Sheet

SURGICAL WICKING DEVICE

CROSS-REFERENCES TO RELATED APPLICATIONS

This application is a continuation-in-part of my application, Ser. No. 08/156,584, filed 23 Nov. 1993, now abandoned of the same SURGICAL ASPIRATION DEVICE.

BACKGROUND OF THE INVENTION

The present invention relates to a novel surgical aspiration device.

In the performance of eye surgery, it is necessary to remove fluids such as irrigating solutions liberally applied to the surgical area. Simple removal of such copious fluids with a swab is inefficient, time consuming, labor intensive, and tends to interfere with surgical procedures. Simple aspiration with a suction device tends to damage soft fragile tissues, such as conjunctiva, during eye surgery, brain matter in cerebral surgery, mesentery during abdominal surgery, and the like. Further, aspiration devices of the prior art are easily clogged with solid particles.

U.S. Pat. No. 5,171,307 reveals an irrigation solution collection device in which fluids are drained from the eye by capillary matting material surrounded by a water impervious sheath. The capillary matting material is taped to the eye and allowed to drain downwardly into a bucket.

U.S. Pat. No. 4,826,478 describes a surgical technique and implant device in which a silicon band is sutured into the sclera of the eye. A tube is mounted into a groove in the band to provide an aqueous pathway in the treatment of glaucoma.

U.S. Pat. No. 5,151,094 shows a suction swab which utilizes a tube that terminates in apertures to allow fluids to be sucked through the apertures to a stem. A tip is formed of pliant foam or other similar soft material to avoid injury of soft tissue in the mouth region of the body. Thus, the soft tip serves as a support for the plurality of holes performing aspiration in a direct manner.

U.S. Pat. No. 3,324,855 teaches a surgical sponge stick which includes a hollow tube handle terminating in a perforated end that is surrounded by a sponge, which serves as a filter for blood. The handle of the sponge stick is connected to a source of suction to aspirate blood directly through the surgical sponge and the tubular handle. The handle is of rigid construction, while the tip of the hollow handle has been flattened to snugly fit within the surgical sponge.

A surgical aspiration device possessing the ability to remove surgical fluids over a large area, without damaging delicate tissues, and without clogging would be a notable advance in the medical field.

SUMMARY OF THE INVENTION

In accordance with the present invention a novel and useful surgical aspiration device is herein provided.

The present invention employs a conduit having a first end portion and a second end portion terminating in an open end. A first end portion of the conduit connects to a suction device for the purpose of aspiration. The second end portion may terminate in an orthogonally cut end or an end which is mitred. In addition, a series of perforations may be constructed at the second end portion to increase the flow of fluids through the second end portion of the conduit. Moreover, the second end portion may be enlarged to adapt to certain surgical applications.

The surgical fluid wicking device of the present invention also includes a porous element which possesses an outer surface enclosing a matrix having an inner reservoir or zone. In certain cases, the inner zone may lie immediately adjacent the outer surface enclosing the matrix. However, the aspiration or suction does not reach the outer surface of the matrix. The porous element is capable of transporting fluids over a large area by transferring fluids from the outer surface to the matrix inner zone solely by capillary flow.

Fastening means is also employed in the present invention for holding the open end of the second end portion of the flexible conduit to the interior of the porous element, adjacent the matrix inner zone. Such fastening means may take the form of heat bonding hollow conduit to the porous element. In addition, fastening means for holding the conduit to the element may take the form of a simple friction fit or the use of a mastic between the same. In addition, such fastening means may be embodied in a cap or elastomeric band which is capable of exerting an inward pressure on the porous element to hold the same to the flexible hollow conduit. Most importantly, fluids brought to the matrix inner zone by capillary flow would be transported therefrom by an aspiration force applied to the conduit. Thus, the aspiration force does not exert an influence through the porous element to the outer surface thereof. In this manner, delicate tissue exposed during surgical procedures is not damaged by the device of the present invention and clogging of the porous element by solids is greatly diminished.

It may be apparent that a novel and useful surgical wicking device has been described.

It is therefore an object of the present invention to provide a surgical fluid wicking device which employs capillary flow to direct fluids extending over a large area at a surgical site to the interior of a porous element for aspiration therefrom.

A further object of the present invention is to provide a surgical fluid wicking device which is not susceptible to clogging by solids such as blood products.

Another object of the present invention is to provide a surgical fluid wicking device which may be employed safely with delicate surgery procedures.

Yet another object of the present invention is to provide a surgical fluid wicking device which removes fluids from a surgical site to permit the surgeon an unobstructed view to the same.

Another object of the present invention is to provide a surgical fluid wicking device which is versatile in application to various types of surgery utilizing irrigating fluids.

A further object of the present invention is to provide a surgical fluid wicking device which requires minimal monitoring during surgery.

Another object of the present invention is to provide a surgical fluid wicking device which is capable of removing blood from wounds without clogging the wicking element employed.

For a better understanding of the invention reference is made to the following detailed description of the preferred embodiments thereof which should be referenced to the prior described drawings.

For a better understanding of the invention, reference is made to the following detailed description of the preferred embodiments thereof which should be taken in conjunction with the prior described drawings.

DETAILED DESCRIPTION OF THE PREFERRED EMBODIMENTS

Various aspects of the present invention will evolve from the following detailed description of the preferred embodiments, and should be referenced to the previously discussed drawings.

Figure 2:
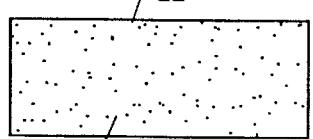
FIG. 2 is a top plan view of the porous element portion of the present invention illustrated in FIG. 1.
Figure 3:
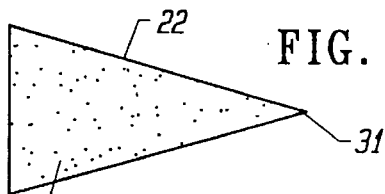
FIG. 3 is a side elevational view of the porous element of the present invention illustrated in FIG. 1.
Figure 4:
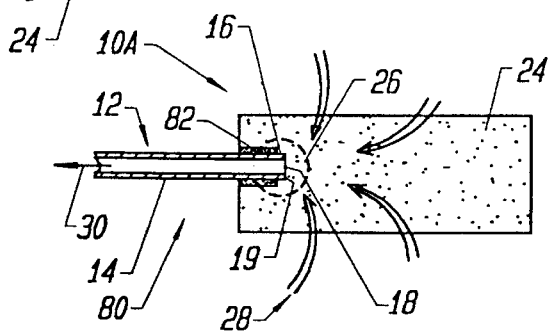
FIG. 4 is a sectional view of a first embodiment of the present invention.

The invention as a whole is depicted in the drawings by reference character 10 with the addition of an upper case letter to denote various embodiments of the same. With reference to FIGS. 2–4, aspiration device 10A is depicted in detail. Wicking device 10A includes as one of its elements a flexible hollow conduit 12. Conduit 12 includes a first end portion 14 and a second end portion 16. For example, conduit 12 may be constructed of plastic tubing approximately 1.5 mm in diameter. First end portion 14 of conduit 12 connects to a standard room source of suction or aspiration (not shown). By way of illustration, Model No. 3020 Aspirator manufactured by Gomco of St. Louis, Mo., suffices in this regard. Second end portion 16 of conduit 12 terminates in an open end 18, which is shown having a flattened end surface 19, FIG. 4.

Porous element 20 is also found in the present device 10. Porous element 20 includes an outer surface 22 and a matrix 24 serving as the core of element 20. Matrix 24 possesses the necessary interstices or pores to permit fluid to pass from outer surface 22 to fluid saturated central zone 26 solely by capillary flow. For example, an open cell sponge constructed of polyvinyl acetate, polypropylene, polytetra-fluoroethylene, polyvinyl chloride and the like may be employed. In the present case, an open cell polyvinyl acetate polymer sponge distributed by Merocel Corp., Mystic, Conn. as Model No. 400200, produces excellent results. Plurality of directional arrows 28, FIG. 4, depict such fluid capillary flow. That is to say, the passage of fluid to central zone 26 of matrix core 24 takes place without the suction force applied to conduit 12, directional arrow 30. It has also been found that porous element 20 is not clogged with solids during use. During use, porous element 20 draws fluid from a wide area outwardly from outer surface 22. Porous element 20 of FIGS. 2–4 is essentially wedged shaped for use in eye surgery, FIG. 1, which will be described in detail hereafter. Tip 31 of porous element 20 may be rounded in certain cases.

Figure 5:
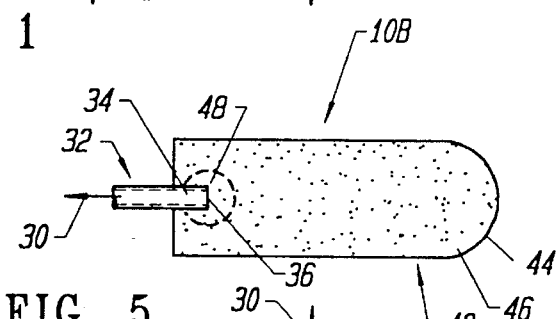
FIG. 5 is a sectional view of a second embodiment of the present invention.

With reference to FIG. 5, it may be observed that a conduit 32 serves as one of the elements of wicking device 10B. Conduit 32 possesses the same flexibility and is constructed of the same material as conduit 12. Conduit 32 includes an end portion 34 having an orthogonally formed end surface 36. Porous element 42, formed of material similar to porous element 20, is cylindrically shaped having a domed end 44. Matrix core 46 of element 42 passes fluid to central zone 48 which is generally spherically shaped. It is believed that embodiment 10B is particularly useful for brain surgery.

Figure 6:
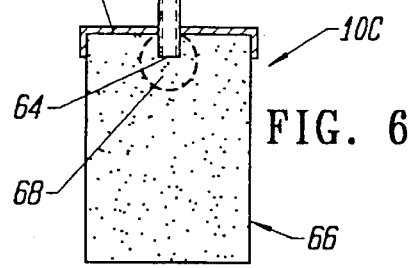
FIG. 6 is a sectional view of a third embodiment of the present invention.

Turning now to FIG. 6, it may be observed that embodiment 10C of the present invention is depicted. Conduit 62 is composed of material similar to conduit 12 and terminates in a straight end portion 64. Porous element 66, or a material similar to porous elements 20, possesses a central zone 68 which immediately surrounds straight end 64 of hollow conduit 62. Porous element 66 is depicted in FIG. 6 as a rectangular solid.

Figure 7:
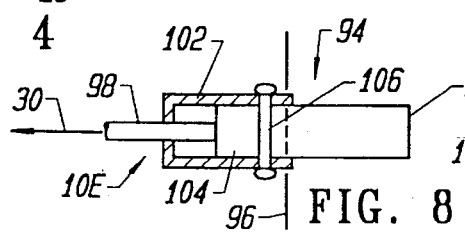
FIG. 7 is a sectional view of a fourth embodiment of the present invention.

With reference now to FIG. 7, embodiment 10D is depicted in which conduit 70 terminates in an orthogonally or square-cut end 72. Rectangular solid porous member 74, or a material similar to porous element 20, possesses a central zone 76. Central zone 76 is spaced from the edge 78 of porous member 74. Cannulae 86 connects conduit 70 to porous member 74. Central zone 76 immediately circumvents the end 73 of cannulae 86.

Fastening means 80 is depicted in the drawings for holding conduits 12, 32, 62, and 70 to porous elements 20, 42, 66, and 74, respectively. With reference to FIG. 4, it may observed that fastening means 80 takes the form of a mastic layer 82 interposed conduit 12 and porous member 20. Turning to FIG. 6, a cap 84 is shown as being fastened to the exterior surface of conduit 62 and to porous element 66 by a friction fit, sonic welding, mastic, or the like. FIG. 7 shows cannulae 86 being fused to porous member 74 to serve as fastening means 80. The embodiment shown in FIG. 5 simply employs a friction fit between conduit 32 and porous members 42.

Figure 8:
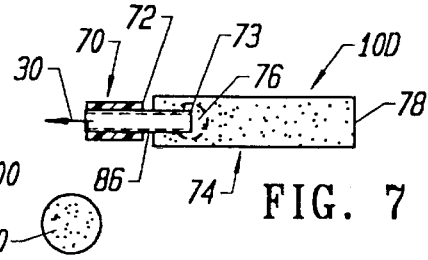
FIG. 8 is a sectional view of a fifth embodiment of the present invention.

FIG. 8 depicts embodiment 10E of the present invention in which porous element 94 is employed. Element 94 is formed of a rapidly wicking continuous aligned fiber polymeric material that has been steam bonded. For example, an 80% void space swab tip, R-1639, distributed by American Filtrona Corp. of Richmond, Va., satisfactorily functions as wicking element 94. Line 96 represents a plane of demarcation between pure capillary wicking, to the right on FIG. 8, and the combination of wicking and aspiration through tube 98, to the left on FIG. 8. Most significantly, end portion 100 of element 94 exerts no aspiration influence when used. Cap 102 holds tube 98 through friction fit to end 104 of element 94. Pin 106 through cap 102 pinions porous element 94 in place.

Figure 1:
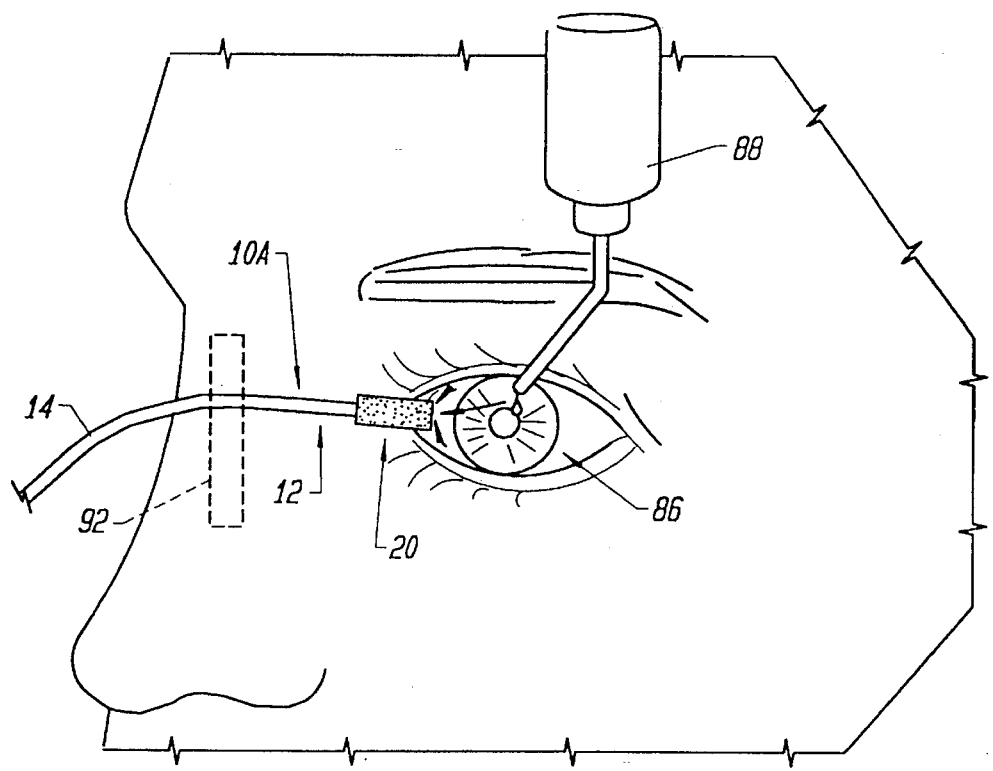
FIG. 1 is a top plan view of the device of the present invention in use during eye surgery.

In operation, FIG. 1, the user would place porous member 20 adjacent eye 86 during eye surgery procedures. Conduit 12 affixes to skin surface 90 by tape 92, although forceps may also be used. Conduit 12, connected to porous member 20, would pass to a source of suction of about 30 inches of mercury or less (not shown). Saline solution or other fluids are passed to eye 86 from bottle 88 at a pre-determined rate to irrigate eye 86 and to maintain an optically clear surface thereat. Device 10A removes such fluid as well as blood, or other bodily fluids while surgery is taking place. Namely, with reference to FIG. 4, fluids would pass through matrix core 24 of porous element 20 by solely capillary flow to central zone 26 thereof. Fluids would then be removed from porous member 20 through open end 18 of conduit 12 according to directional arrow 30. It should be noted that the suction force found at the open end 18 of conduit 12 is only capable of removing fluids from inner or central zone 26 and does not exert a force on outer surface 22 of porous member 20. In this manner, conjunctiva, in the case of eye surgery, is not harmed in any manner by device 10. In addition, porous element 20 is not occluded by solids. Embodiment 10B–10D operate in a similar manner in removing irrigating solutions, blood, and blood products from surgical sites after such fluids pass to central zones 48, 68, and 76, of embodiments 10B, 10C, 10D.

Similarly, when embodiment 10E is pressed into contact with the above mentioned fluids, end portion 100 wicks said fluid to end portion 104, where aspiration, directional arrow 30 takes place. Aspiration within end portion 100 does not occur, i.e. to the right of line 96 on FIG. 8. It should be noted that the porous element of FIG. 7 may be formed of a material similar to element 94 of FIG. 8. Thus, the reservoir or zone of embodiment 10E lies to the left of line 96, FIG. 8.

The following examples are provided to further illustrate the invention herein, but are not deemed to limit the same:

EXAMPLE I

The embodiment 10A shown in FIGS. 1–4 of the drawings was employed during eye surgery. Wicking by element 20 was observed independently of any aspiration through the aspiration tube. Subsequently, approximately a vacuum of 20–22 inches of mercury was applied to tube 14 while saline solution was continually distributed on a human eye. Saline solution was removed from the surgery area without damage to the conjunctiva.

EXAMPLE II

The embodiment of the present invention 10A of FIGS. 1–5 was employed during eyelid surgery to remove blood from the wound. The wicking element 20 was placed adjacent a human eyelid during this process. The wicking of blood from blood coagulates was observed independent of aspiration. Clogging of the wicking element by blood coagulates did not occur during this process.

EXAMPLE III

Figure 9:
FIG. 9 is an end view of the embodiment illustrated in FIG. 8.

The device of FIGS. 8 and 9 was employed to wick fluids and to test the influence of aspiration. 30 inches of mercury was applied to aspiration tube 98 of embodiment 10E of the present invention. The end portion 100 was interrupted by the finger of the user. The indication of the aspiration pressure did not change during such blockage, indicating that aspiration is not occurring at end portion 100 of embodiment of 10E.

EXAMPLE IV

The embodiments of FIGS. 1–4 and FIG. 7, using the polyvinyl acetate of element 20 and the steam bonded polyolefin of element 94 was attached to a Gomco suction apparatus. The vacuum level was adjusted to 30" of Hg. A Weiss manometer was attached to a PVC tubing and terminated in a 16 gage blunt tipped needle. The needle served as a probe to test for vacuum on all surfaces of the porous elements. The needle then penetrated the porous elements. A vacuum registered only when the needle was within less than 1 mm from the aspiration conduit within the particular porous element. It was concluded the influence of the aspiration only occurred in the very near vicinity of the aspiration tube within the particular porous element.

While, in the foregoing, embodiments of the present invention have been set forth in considerable detail for the purposes of making a complete disclosure of the invention, it may be apparent to those of skill in the art that numerous changes may be made in such details without departing from the spirit and principles of the invention.

What is claimed is:

1. A surgical fluid aspiration device, comprising:
   a. means for providing a suction force;
   b. a conduit having a first end portion and a second end portion, terminating in open end, said first end portion being connected to the means for providing a suction force;
   c. a porous element possessing an outer surface and a matrix within, said matrix having an inner zone spaced from said outer surface, said porous element being capable of transporting fluids from said outer surface to said matrix inner zone by capillary flow only;
   d. fastening means for holding said open end of said second end portion of said conduit to the interior of said porous element adjacent said matrix inner zone to permit flow of fluids from said matrix inner zone to said conduit only by the influence of the suction force; and
   e. means for determining the magnitude of the suction force of the means for providing a suction force, to provide the suction force only to said inner zone of said porous element.

2. The device of claim 1 in which said conduit open end includes an angled end surface.

3. The device of claim 1 in which said fastening means comprises a mastic interposed said conduit and said porous element.

4. The device of claim 1 in which said fastening means includes a bracket overlying a portion of said porous element and connected thereto said bracket contacting said conduit.

5. The device of claim 1 in which said second end portion of said conduit includes an enlargement.

6. The device of claim 1 in which said porous element further comprises a soft outer surface.

7. The device of claim 1 in which said porous element further comprises a bonded continuous fiber polymeric material.

8. The device of claim 1 in which said fastening means comprises heat fusion of said conduit to said porous element.

* * * * *